United States Patent [19]

Okinaka et al.

[11] 4,045,178
[45] Aug. 30, 1977

[54] REDUCING GAS SENSOR

[75] Inventors: Hideyuki Okinaka, Setsu; Atsushi Iga, Tatatsuki; Masatake Ayusawa; Masatugu Yamaguchi, both of Hirakata; Seiichi Nakatani, Kadoma; Toshiaki Yagami, Shijyonawate, all of Japan

[73] Assignee: Matsushita Electric Industrial Co., Ltd., Japan

[21] Appl. No.: 738,745

[22] Filed: Nov. 3, 1976

[30] Foreign Application Priority Data

| Nov. 8, 1975 | Japan | 50-134285 |
| Nov. 8, 1975 | Japan | 50-134286 |
| Nov. 8, 1975 | Japan | 50-134287 |
| Nov. 11, 1975 | Japan | 50-135772 |
| Nov. 11, 1975 | Japan | 50-135773 |
| Nov. 13, 1975 | Japan | 50-136941 |

[51] Int. Cl.$^2$ .......................... G01N 27/12
[52] U.S. Cl. .......................... 23/254 E
[58] Field of Search .......... 23/254 E, 232 E; 338/34; 340/237 R; 73/23, 27

[56] References Cited

U.S. PATENT DOCUMENTS 3,695,848  10/1972  Taguchi .................. 23/254 E

OTHER PUBLICATIONS

Seiyama et al, Anal. Chem. 38, 1069 (1966).

*Primary Examiner*—Robert M. Reese
*Attorney, Agent, or Firm*—Wenderoth, Lind & Ponack

[57] ABSTRACT

This invention provides a reducing gas sensor which has a gas sensitive element composed of, as a main constituent, $\gamma$-ferric oxide ($\gamma$-$Fe_2O_3$) and, as an additive, at least one compound in the group of $WO_3$, $MoO_3$, $SiO_2$, $GeO_2$, $Li_2O$, $Na_2O$, $K_2O$, $CaO$, $SrO$, $BaO$, $Eu_2O_3$, $La_2O_3$, $CeO_2$, $Al_2O_3$, $Ga_2O_3$, $In_2O_3$, $SnO_2$, $TiO_2$, $MgO$, $NiO$, $ZnO$, $Mn_2O_3$ and $Cr_2O_3$, a pair of electrodes and a heater element. The $\gamma$-ferric oxide is in the form of a thin film, a plate or a thin surface layer on a sintered plate of $\gamma$-ferric oxide. The gas sensor of the invention is much improved in the stability during use and also it has a high sensitivity.

11 Claims, 4 Drawing Figures

Amount of SrO (mol %)

Amount of $WO_3$ (mol %)

REDUCING GAS SENSOR

This invention relates to a reducing gas sensor comprising a gas sensitive element, a pair of electrodes applied of the sensitive element and a heater element.

Several materials are known to be sensitive to reducing gases and have been used in the reducing gas sensor as sensitive elements. They undergo a change in properties (e.g. color, electrical resistance, etc.) upon coming in contact with an atmosphere containing a reducing gas.

Among the known gas sensitive materials used in a reducing gas sensor, recently several metal oxide semiconductors have been used as gas sensitive elements. The metal oxides of N-type semiconductors undergo a rapid decrease in electrical resistance upon coming in contact with a reducing gas. The change of electrical resistance of the semiconductors is reversible. A reducing gas sensor using such semiconductors has a simple structure and has high sensitivity.

One of these semiconductors is stannic dioxide disclosed by U.S. Pat. No. 3,695,848. The stannic dioxide gas sensitive element has high sensitivity but has several disadvantages such as a large temperature dependence of the electrical resistance and a decrease of the sensitivity at an elevated temperature up to 300° C and also a short lifetime. Other known semiconductors include zinc oxide (ZnO) and/or cadmium oxide (CdO). The sensitivity of a sensitive element of (ZnO) or (CdO) is fairly low. Still other known semiconductors include titanium dioxide ($TiO_2$), ferric oxide ($Fe_2O_3$), alumina ($Al_2O_3$), tungsten trioxide ($WO_3$) and molybdenum trioxide ($MoO_3$). However, the change of the electrical resistivity of these materials exposed to an atmosphere containing a reducing gas can be scarcely observed, as taught by the Journal of Analytical Chemistry, 38 (8) 1069 (1966). Therefore, these materials have not been used as sensitive elements in a reducing gas sensor.

One of the inventors of the present application has filed with co-inventors U.S. application Ser. No. 618,680 in which there is disclosed a novel reducing gas sensor comprising a gas sensitive element composed of $\gamma$-ferric oxide ($\gamma$-$Fe_2O_3$) and method of producing that gas sensor.

According to the above mentioned earlier application, the reducing gas sensor comprises a gas sensitive element composed mainly of $\gamma$-ferric oxide ($\gamma$-$Fe_2O_3$), a pair of electrodes applied to the sensitive element and a heater element, for heating the gas sensitive element, so that the gas sensitive element at an elevated temperature undergoes a rapid decrease in electrical resistance upon coming in contact with an atmosphere containing a reducing gas. According to the method of that application, an iron oxide is fired at a temperature between 100° C and 600° C for 30 minutes to 5 hours in an oxidizing atmosphere to obtain a sintered $\gamma$-ferric oxide ($\gamma$-$Fe_2O_3$) as a gas sensitive element, a pair of electrodes are applied to the gas sensitive element and a heater element is placed near the gas sensitive element.

There are many types of crystal structure of ferric oxide ($Fe_2O_3$). They are alpha-ferric oxide ($\alpha$-$Fe_2O_3$), beta-ferric oxide ($\beta$-$Fe_2O_3$), gamma-ferric oxide ($\gamma$-$Fe_2O_3$), delta-ferric oxide ($\delta$-$Fe_2O_3$), epsilon-ferric oxide ($\epsilon$-$Fe_2O_3$) and eta-ferric oxide ($\eta$-$Fe_2O_3$). Alpha-ferric oxide is mostly used as a raw material in various industries. Therefore, the unmodified expression ferric oxide usually means $\alpha$-ferric oxide ($\alpha$-$Fe_2O_3$), which has a corundum type of crystal structure. Beta, delta, epsilon and eta-ferric oxides have hardly ever been used in industry.

Gamma-ferric oxide ($\gamma$-$Fe_2O_3$) has been used as a magnetic recording media for a magnetic recording tape or disk. $\gamma$-$Fe_2O_3$ has a spinel type of crystal structure and it has been called magnemite, gamma hematite, or gamma ferric oxide, but it has never been called merely hematite or ferric oxide, because it is quite different from $\alpha$-$Fe_2O_3$. One is magnetic, the other is non-magnetic.

The gas sensor of $\gamma$-$Fe_2O_3$ of the above mentioned earlier application has higher sensitivity than those employing the other types of ferric oxides. That is, as described in the above mentioned earlier application, each of the various types of ferric oxides in powder form is mixed with water in a ball mill to form a slurry which is a homogeneous mixture, and the mixture is applied as a thin film on an insulator substrate e.g. of alumina and heated e.g. at 400° C for 1 hour in air. Then, a pair of electrodes are applied to the thin film, and the sensitivity is measured. The sensitivity of the iron oxide as a gas sensitive element of a reducing gas sensor is defined as the ratio of the electrical resistance in air to that in an atmosphere containing a reducing gas at an elevated temperature. The electrical resistances of the gas sensitive element are $R_A$ in air and $R_G$ in an atmosphere containing a reducing gas. The value of the ratio ($R_A/R_G$) indicates the sensitivity of the gas sensitive element. The electrical resistances are measured in air and in an atmosphere containing e.g. 1 volume percent of propane gas e.g. at 300° C. The sensitivity ($R_A/R_G$) of the $\gamma$-$Fe_2O_3$ is about 10 to about 130. On the other hand, the sensitivity of the $\alpha$-$Fe_2O_3$ is about 2 to about 5. Futhermore, the $\alpha$-$Fe_2O_3$ has an extremely high electrical resistivity. The sensitivities of the gas sensitive elements of other types of ferric oxides (e.g. $\beta$-$Fe_2O_3$, $\delta$-$Fe_2O_3$, $\epsilon$-$Fe_2O_3$ and $\eta$-$Fe_2O_3$) are about 1 to about 5. Extremely high values of sensitivity are observed in only $\gamma$-type ferric oxide.

As described above, the gas sensor of $\gamma$-$Fe_2O_3$ has a high sensitivity, but still there is a demand for improving stability in practical use of the gas sensor of $\gamma$-$Fe_2O_3$. In order to prevent explosion and erroneous operation, a gas sensor for detecting leakage of gas is required to have a quick response and a very high stability of operation. That is, a gas sensitive element should be operted stably at an elevated temperature for realizing a quick response, and the resistance at such an elevated temperature should not be changed so much.

However, $\gamma$-$Fe_2O_3$ is an unstable phase at a high temperature. When it is left at a high temperature for a long time, by phase transition it becomes $\alpha$-$Fe_2O_3$ which is stable even at a high temperature. This phase transition from $\gamma$-phase to $\alpha$-phase is irreversible. Once $\gamma$-$Fe_2O_3$ changes to $\delta$-$Fe_2O_3$, it is very difficult to change $\alpha$-$Fe_2O_3$ to the original $\gamma$-$Fe_2O_3$. As described hereinbefore, the sensitivity of $\alpha$-$Fe_2O_3$ to a reducing gas is very low, and further the $\alpha$-$Fe_2O_3$ has an extremely high electrical resistivity. Therefore, the phase transition from $\gamma$-$Fe_2O_3$ to $\alpha$-$Fe_2O_3$ in the gas sensitive element makes it impossible to use the element for the gas sensor any more.

Therefore, it is an object of the present invention to provide a reducing gas sensor which has high stability during use.

It is another object of the present invention to provide an improved reducing gas sensor of $\gamma$-$Fe_2O_3$ with additives which has high stability during use without degrading its high sensitivity.

These objects are achieved by providing a reducing gas sensor according to the present invention, which comprises a gas sensitive element composed of, as a main constitutent, γ-ferric oxide (γ-$Fe_2O_3$) and, as an additive, at least one member selected from the group consisting of $WO_3$, $MoO_3$, $SiO_2$, $GeO_2$, $Li_2O$, $Na_2O$, $K_2O$, CaO, SrO, BaO, $Eu_2O_3$, $La_2O_3$, $CeO_2$, $Al_2O_3$, $Ga_2O_3$, $In_2O_3$, $SnO_2$, $TiO_2$, MgO, NiO, ZnO, $Mn_2O_3$ and $Cr_2O_3$, a pair of electrodes on said sensitive element and a heater element adjacent said element, whereby when said gas sensitive element is heated to an elevated temperature it undergoes a rapid decrease in electrical resistance upon coming in contact with an atmosphere containing a reducing gas.

These and other objects and features of this invention will be apparent upon consideration of the following description taken together with the accompanying drawings, in which.

Figure 1:
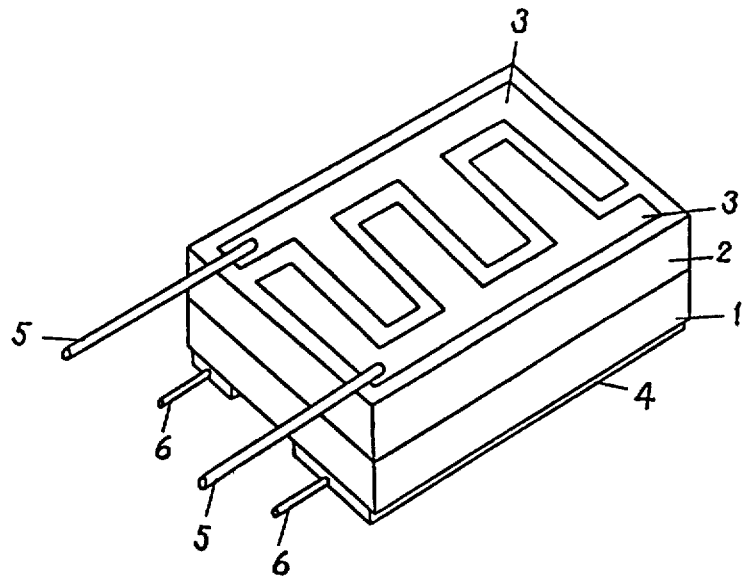
FIG. 1 is a perspective view of an example of a reducing gas sensor contemplated by this invention.

During use of the reducing gas sensor of γ-$Fe_2O_3$, from the standpoint of sensitivity and response speed, it is necessary to keep the gas sensitive element at an elevated temperature. As described hereinbefore, γ-$Fe_2O_3$ changes to α-$Fe_2O_3$ by phase transition at a high temperature. Further, even at a temperature lower than the phase transition temperature, when it is left for a long time, phase transition is caused gradually. Each of the γ-$Fe_2O_3$ produced by several methods disclosed in the aforesaid earlier application has a phase transition temperature of at most 630° C. Therefore, it is necessary to increase the phase transition temperature of γ-$Fe_2O_3$ to have a stable and practical γ-$Fe_2O_3$ gas sensor The inventors have studied various modified compositions of γ-$Fe_2O_3$ as the gas sensitive element and found that some particular additives are very effective to improve the stability of the γ-$Fe_2O_3$ gas sensor. The gas sensitive element of the invention composed, as a main constituent, of γ-ferric oxide (γ-$Fe_2O_3$) and the additive is produced, in principle, by the similar methods to those disclosed in the aforesaid earlier application. The modified γ-ferric oxide with the additive, when used as a gas sensitive element in a reducing gas sensor, can have the form of a sintered body. This sintered body can be in the form of a thin film, a plate, a thin surface layer on sintered γ-$Fe_2O_3$, etc. The sintered body of γ-ferric oxide is superior in mechanical strength and stability as a gas sensitive element.

This invention will be more readily understood with reference to the following Examples, but these Examples are intended to illustrate this invention only, and are not to be construed to limit thereby the scope of this invention.

EXAMPLE 1

1 mol of $FeCl_2$, 2 mol of $FeCl_3$ and 0.015 mol of $SrCl_2$ are dissolved in one liter of distilled water, and the resultant solution is dripped (added) gradually in mixed solution of 16 mol of NaOH and 1 liter of distilled water. At this time, there is caused the following reaction:

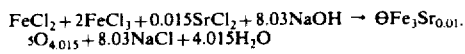

$FeCl_2 + 2FeCl_3 + 0.015SrCl_2 + 8.03NaOH \rightarrow \Theta Fe_3Sr_{0.01}$
$.5O_{4.015} + 8.03NaCl + 4.015H_2O$ Although the necessary amount of NaOH is 8.03 mol according to the above reaction formula, excess NaOH is added so as to lower deviation of $H^+$ concentration (pH). In order to keep a constant pH value, it is also possible to supply NaOH by the amount corresponding to that consumed, while adding the solution.

After the addition the solution is filtered and the precipitate is cleaned by decantation. When the $Cl^-$ density in the cleaning water becomes lower than $5 \times 10^{-5}M$, the cleaning is stopped and the solution is filtered. Then, the resultant precipitate is dried in a drier at a temperature of 80° to 100° C for 4 to 10 hours. The dried product is pulverized by a mortar, and the resultant powder is subjected to an oxidation treatment by heating at a temperature of 300 to 400° C for 1 to 3 hours. Thus, there is provided Sr-modified γ-$Fe_2O_3$.

By chemical analysis of the thus provided γ-$Fe_2O_3$, it is found that 0.89 mol % of SrO is contained therein. Further, presence of α-$Fe_2O_3$ is not recognized by X-ray powder diffraction observation, and the phase transition temperature from γ-$Fe_2O_3$ to α-$Fe_2O_3$ is found to be 680° C by differential thermal analysis.

The thus obtained Sr-modified γ-$Fe_2O_3$ is finely pulverized and mixed with organic binder in paste. The paste is applied on the surface of an alumina substrate of 5mm × 5mm 0.5mm as a film of 20 microns thickness.

Then, the film bearing substrate is heated by gradually increasing the temperature not so as to cause a crack on the applied film and kept at 350° C for 2 hours, and it is then cooled. After firing the Sr-modified γ-$Fe_2O_3$ film, comb electrodes are formed thereon by evaporating gold on the film. On the other surface of the alumina substrate, a platinum heater is attached, and the whole body is covered with a stainless steel cap of 100 mesh. Thus, a reducing gas sensor is completed.

Referring to FIG. 1 which shows a perspective view of the gas sensor formed as described above, the gas sensor comprises the gas sensitive film designated by a reference numeral 2 formed on the substrate 1, a pair of electrodes 3, lead wires 5 attached to the electrodes 3, the platinum heater 4 attached to the other surface of the substrate 1, and lead wires 6 attached to the heater 4. In FIG. 1, the steel cap is omitted.

The gas sensitive film 2 is kept at 300° C by the heater 4, and the resistance $R_A$ between the electrodes 3 is measured in air. $R_A$ is 1.65 MΩ. Then, the sensor is put in an atmosphere of air contaning 1 vol % propane, and the resistance $R_G$ in that atmosphere is measured. $R_G$ is 28.0 KΩ, remarkably reduced compared with $R_A$. In this case, the sensitivity $R_G/R_A$ is 58.9. Then, current to the heater 4 is switched off, and the gas sensor is held in an electric furnace kept at 400° C for 1000 hours. After 1000 hours, the heater 4 is again switched on and the film 2 is kept at 300° C. Then, similarly the resistances $R_A$ and $R_G$ are measured. $R_A$ is 1.83 MΩ and $R_G$ is 27.5 KΩ, and so the sensitivity is 66.5. These results show that the gas sensor has a high stability, even when it is kept at the high temperature of 400° C for 1000 hours.

EXAMPLE 2

Figure 3:
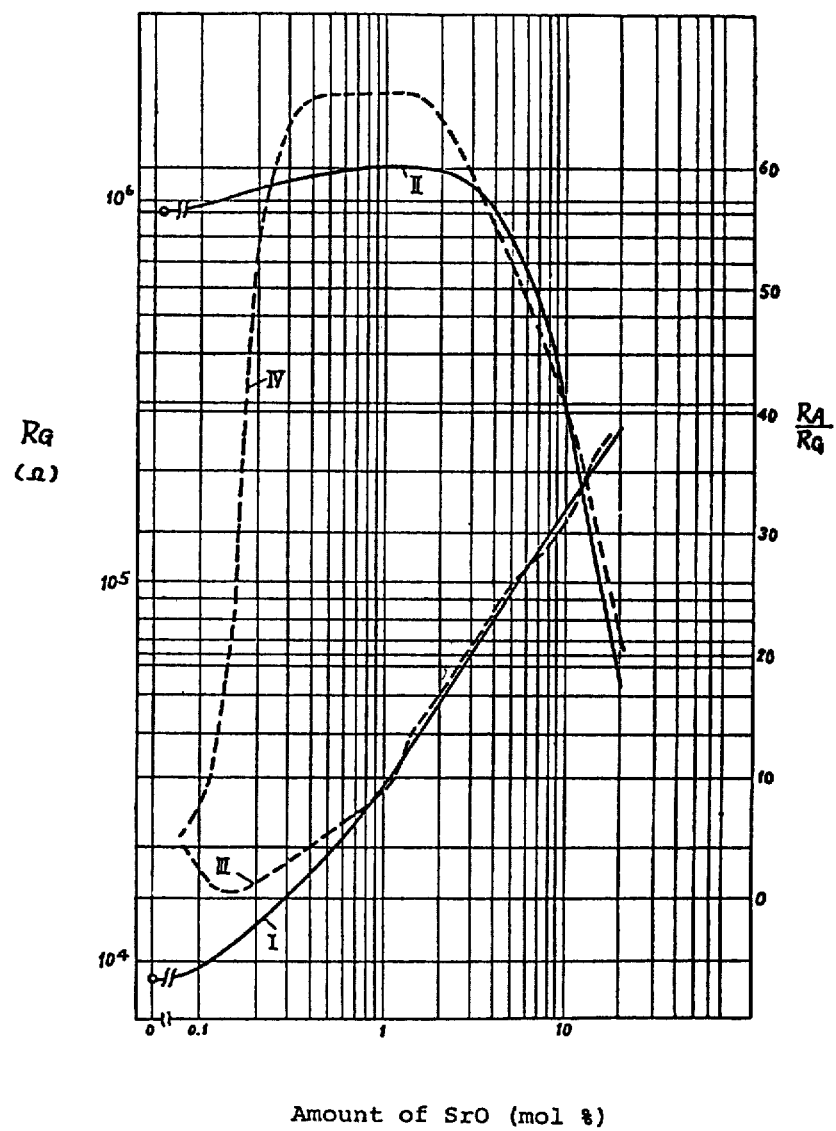
FIG. 3 is a graph showing the relation between the electrical resistances of the reducing gas sensor according to FIG. 1 (kept at 300° C in air containing propane) and the amount of added SrO.

With the same procedure as that of Example 1, various samples are made by changing the amount of added $SrCl_2$. The characteristics of the resultant gas sensors are measured under the same conditions as those of Example 1. The results are shown in FIG. 3 and Table 1. FIG. 3 is a graph showing relation between amount of SrO and the resistance $R_G$ and between amount of SrO and the sensitivity $R_A/R_G$. Curve I is the initial resistance $R_G$ in air containing 1 vol % propane, and curve II is the initial sensitivity. After the sensor is held at 400° C for 1000 hours, the resistance $R_G$ and the sensitivity are depicted as curves III and IV, respectively. As obvious from FIG. 3, with an amount of SrO less than 0.1 mol %, stability is poor, and with an amount of SrO more than 20.0 mol %, the sensitivity is largely degraded. With the addition of SrO in amount of 0.1 to 20.0 mol %, the stability of the gas sensor is much improved and the sensitivity is high.

EXAMPLE 3

Similarly to Example 1, various kinds of modified $\gamma\text{-}Fe_2O_3$ are produced using other additives instead of SrO. They include $WO_3$, $MoO_3$, $SiO_2$, $GeO_2$, $Li_2O$, $Na_2O$, $K_2O$, CaO, BaO, $Eu_2O_3$, $La_2O_3$, $CeO_2$, $Al_2O_3$, $Ga_2O_3$, $In_2O_3$, $SnO_2$, $TiO_2$, MgO, NiO, ZnO, $Mn_2O_3$ and $Cr_2O_3$. In this case, the starting materials for these additives are corresponding chlorides, similarly to Example 1. For example, for the additive CaO, the starting materials are $FeCl_2$, $FeCl_3$ and $CaCl_2$. All of the gas sensors using $\gamma\text{-}Fe_2O_3$ modified with one of these additives show improved high stability and sensitivity, similar to Examples 1 and 2. Table 1 shows some of the measured data of the electrical resistance in air contaning 1 vol % propane and the initial sensitivity as well as the sensitivity after heating at 400° C For 1000 hours. The resistances are measured upon heating the gas sensitive film to 300° C, similarly to Example 1.

According to the results of the experiments, the preferred amount of the additive varces according to the kkind of the additive. That is, the preferred amount of $WO_3$, $MoO_3$, $SiO_2$ and $GeO_2$ is 0.1 to 40 mol %, that of $Li_2O$, $Na_2O$ and $K_2O$ is 0.1 to 10 mol %, that of CaO, BaO, $Eu_2O_3$, $La_2O_3$, $CeO_2$, $Al_2O_3$, $Ga_2O_3$ and $In_2O_3$ is 0.1 to 20.0 mol %, similar to that of SrO as described in Example 2, that of $SnO_2$ and $TiO_2$ is 0.1 to 30 mol %, and that of MgO, NiO, ZnO, $Mn_2O_3$ and $Cr_2O_3$ is 0.1 to 15 mol %.

EXAMPLE 4

Similarly to Example 1, some kinds of modified $\gamma\text{-}Fe_2O_3$ are produced using the other two additives instead of the single additive SrO. Table 2 shows some of the data which are measured upon heating the gas sensitive film at 300° C similarly to Example 1. Although Table 2 shows only some cases, it is confirmed by many experiments that the combination of any two additives described in Example 3 is effectively used as the gas sensor of the invention. In this case, preferred total amount of the two additives is similar to that of the single additive. For example, when employing $SiO_2$ and $TiO_2$ shown in Table 2, the preferable total amount is 0.1 to 30.0 mol %. When employing SrO and MgO, for example, each having a different preferred range, the preferred total amount is selected according to the wider range. In the above case of SrO and MgO, that amount is 0.1 to 20.0 mol %.

Further, it is confirmed by experiments that combination of additives of more than any two additives from the group described in Example 3 is also effectively used for the gas sensor of the invention, although all of the possible combinations have not been actually experimented with because of infinite number of combinations. Table 3 shows one example of the combination of three additives of $Eu_2O_3$, $La_2O_3$ and $CeO_2$. The preferred amount of all of these three additives is also 0.1 to 20.0 mol % from the standpoint of stability and sensitivity.

EXAMPLE 5

Figure 2:
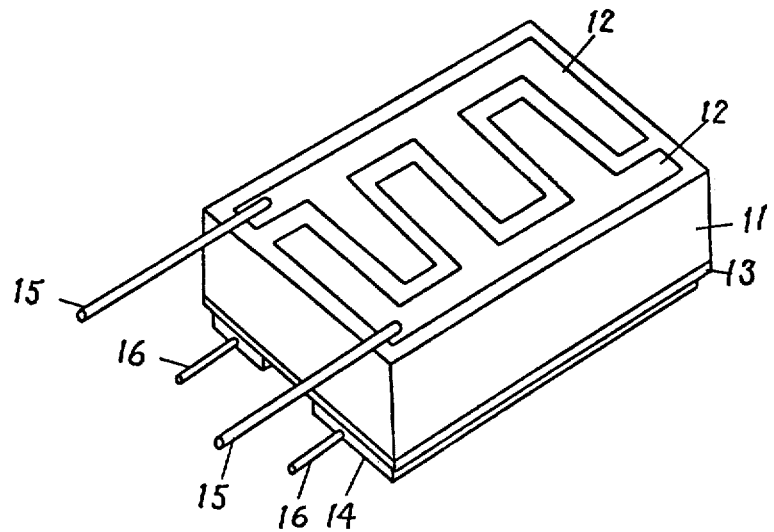
FIG. 2 is a perspective view of another example of a reducing gas sensor contemplated by this invention.

0.9 mol of $Fe_3O_4$ powder and 0.1 mol of $WO_3$ powder, each having average particle size of 0.1 micron, are mixed with water. The mixture is well pulverized and mixed. After the mixed powder is dried in vacuum at room temperature, it it compressed into a square form. Then, the compressed body is sintered at 750° C in a flow of nitrogen gas. After the sintered body is cooled, it is gradually heated and kept at 400° C in oxidizing atmosphere. Then, there is provided a sintered body comprising $\gamma\text{-}Fe_2O_3$ as a main constituent. As shown in FIG. 2, on the surface of the thus obtained sintered body 11, a pair of electrodes 12 are formed by evaporating gold. On the other surface of the sintered body 11, platinum heater 14 is attached with inorganic adhesive 13. Then, lead wires 15 and 16 are attached to the electrodes 12 and the heater 14, respectively. By covering the thus obtained whole body with a stainless steel cap, which is omitted in FIG. 2, the gas sensor is completed.

While maintaining the gas sensitive element employing sintered body 11 at 350° C by heater 14, the resistance $R_A$ between the electrodes in air and the resistance $R_G$ in air contaning 0.5 vol % iso-butane are measured. $R_A$ is 75.1 K and $R_G$ is 2.28 K$\Omega$, and so the sensitivity $R_A/R_G$ is 32.9. Then current to the heater 14 is switched on, and the gas sensor is held at 400° C for 1000 hours. After that, the resistances $R_A$ and $R_G$ are measured under the same conditions. $R_A$ is 81.3K$\Omega$ and $R_F$ is 2.43 K$\Omega$, and so the sensitivity is 33.5. It is understood that the gas sensor has a high stability and sensitivity.

EXAMPLE 6

Figure 4:
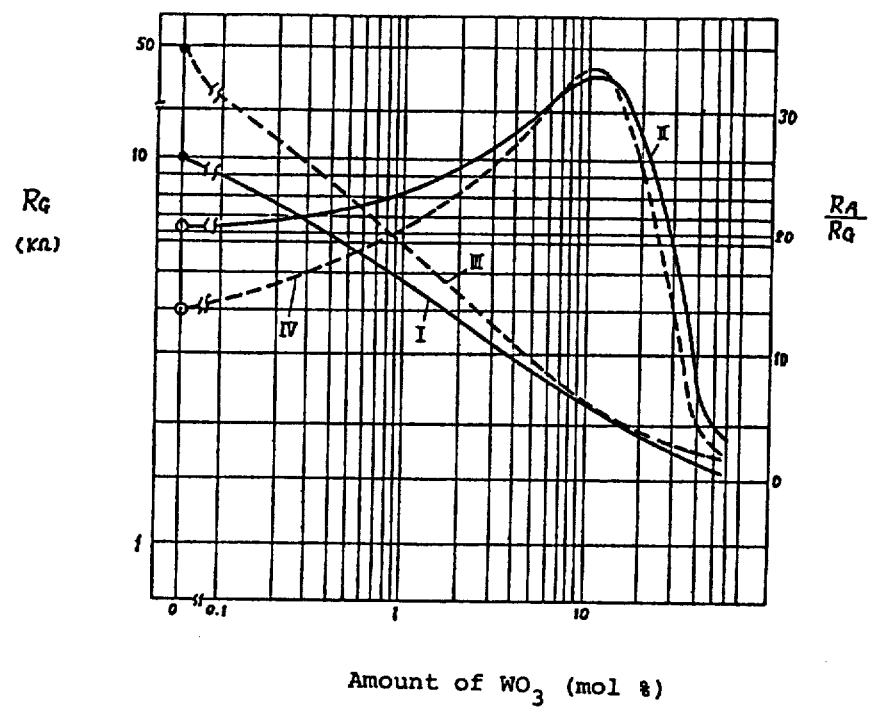
FIG. 4 is a graph showing the relation between the electrical resistances of reducing gas sensors of FIG. 2 (kept at 350° C in air containing isobutane) and the amount of added $WO_3$.

With the same procedure as that of Example 5, various samples are made by changing the amount of added $WO_3$. The characteristics of the resultant gas sensors are measured under the same conditions as those of Example 5. The results are shown in FIG. 4 and Table 4. FIG. 4 is a graph showing relations between amount of $WO_3$ and the resistance $R_G$ and between amount of $WO_3$ and the sensitivity $R_A/R_G$. Curve I depicts the initial resistance $R_G$ in air contaning 0.5 vol % isobutane, an A curve II depicts the initial sensitivity. After the sensor is held at 400° C for 1000 hours, the resistance $R_G$ and the sensitivity is depicted as curves III and IV, respectively. As obvious from FIG. 4, with the amount of $WO_3$ less than 0.1 mol % stability is poor, and with the amount of $WO_3$ more than 40.0 mol %, the sensitivity is largely degraded. With the additon of $WO_3$ in amount of 0.1 to 40.0 mol %, the stability of the gas sensor is much improved and the sensitivity is high.

EXAMPLE 7

Similarly to Example 5, various kind of modified $\gamma\text{-}Fe_2O_3$ are produced using the other additives instead of $WO_3$. Also in the case of using the sintered body as the gas sensitive element, all of the gas sensors using $\gamma\text{-}Fe_2O_3$ modified with one of the additives as described in Example 3 show improved high stability and sensitivity, similarly to Examples 5 and 6. Table 4 shows some of the measured data of the electrical resistance in air containing 0.5 vol % isobutane and the sensitivity at initial and after heating at 400° C for 1000 hours, for some of the above mentioned additives. The resistances are measured upon heating the gas sensitive sintered body to 350° C similarly to Example 5. Also in this case, the preferred amount of each the additives is the same as that of the aforesaid Examples using the modified γ-Fe₂O₃ film as the gas sensitive element.

EXAMPLE 8

Similarly to Example 5, some kinds of modified γ-Fe₂O₃ are produced using the other two additives instead of the single additive of $WO_3$. Table 5 shows some data which are measured upon heating the gas sensitive sintered body at 350° C similarly to Example 5. Although Table 5 shows only some cases, it is confirmed by many experiments that the combination of any two additives described in Example 3 is effectively used for the gas sensor of the invention. In this case, preferred total amount of the two additives is similar to that of the single additive. For example, in case of adding $WO_3$ and $MoO_3$ shown in Table 2, the preferred total amount is 0.1 to 40.0 mol %. In case of adding SrO and MgO, for example, each having a different preferred range, the preferred total amount is selected according to the wider range. In the above case of SrO and MgO, that amount is 0.1 to 20.0 mol %.

Further, it is confirmed by experiments that combination of more than any two additives from the group described in Example 3 is also effectively used for the gas sensor of the invention, although all of the possible combinations have not been actually experimented with because of the infinite number of combinations. Table 6 shows one example of the combination of three additives of $Li_2O$, $Na_2O$ and $K_2O$. The preferred amount of all of these three additives is also 0.1 to 10.0 mol % from the standpoint of stability and sensitivity.

Table 1

| Additives (mol %) | | Sensitivity ($R_A/R_G$) | Electrical resistance in air containing 1 Vol. % Propane ($R_G$) | after heating at 400° C for 1000 hrs | |
|---|---|---|---|---|---|
| | | | | $R_A/R_G$ | $R_G$(KΩ) |
| SrO | 0.1 | 58.2 | 9.8 | 7.5 | 17.9 |
| | 0.5 | 59.8 | 18.9 | 66.0 | 21.7 |
| | 1.0 | 59.0 | 28.0 | 66.2 | 27.8 |
| | 5.0 | 54.0 | 95.0 | 51.8 | 98.2 |
| | 10.0 | 40.4 | 155.1 | 40.6 | 142.6 |
| | 20.0 | 18.5 | 252.1 | 22.2 | 264.4 |
| CaO | 0.1 | 59.3 | 10.6 | 9.6 | 19.2 |
| | 0.5 | 58.5 | 21.1 | 56.4 | 24.6 |
| | 1.0 | 59.1 | 32.3 | 56.8 | 33.2 |
| | 5.0 | 53.6 | 93.0 | 50.3 | 58.2 |
| | 10.0 | 42.4 | 151.7 | 38.8 | 145.7 |
| | 20.0 | 26.5 | 245.7 | 29.2 | 228.4 |
| BaO | 0.1 | 56.9 | 8.8 | 15.3 | 13.2 |
| | 0.5 | 61.8 | 15.6 | 62.1 | 17.3 |
| | 1.0 | 62.2 | 23.4 | 62.7 | 22.8 |
| | 5.0 | 58.5 | 80.0 | 59.0 | 73.8 |
| | 10.0 | 52.6 | 134.9 | 54.4 | 123.2 |
| | 20.0 | 34.5 | 219.4 | 34.3 | 206.2 |
| SnO₂ | 0.1 | 56.1 | 9.2 | 34.6 | 11.8 |
| | 0.5 | 55.8 | 13.0 | 39.9 | 13.7 |
| | 1.0 | 55.4 | 15.7 | 39.6 | 16.1 |
| | 5.0 | 53.5 | 29.3 | 37.5 | 28.0 |
| | 10.0 | 51.2 | 41.0 | 35.7 | 38.0 |
| | 20.0 | 44.4 | 61.7 | 30.2 | 54.1 |
| | 30.0 | 28.7 | 86.4 | 15.6 | 70.7 |
| TiO₂ | 0.1 | 68.2 | 39.5 | 58.4 | 41.3 |
| | 0.5 | 69.1 | 62.3 | 71.2 | 62.5 |

Table 1-continued

| Additives (mol %) | | Sensitivity ($R_A/R_G$) | Electrical resistance in air containing 1 Vol. % Propane ($R_G$) | after heating at 400° C for 1000 hrs | |
|---|---|---|---|---|---|
| | | | | $R_A/R_G$ | $R_G$(KΩ) |
| | 1.0 | 65.6 | 61.1 | 64.3 | 60.7 |
| | 5.0 | 58.6 | 43.2 | 59.9 | 43.5 |
| | 10.0 | 36.9 | 21.9 | 37.5 | 20.3 |
| | 20.0 | 32.4 | 15.3 | 31.8 | 15.2 |
| | 30.0 | 20.3 | 14.1 | 20.0 | 14.4 |
| Eu₂O₃ | 0.1 | 56.6 | 10.2 | 13.3 | 17.4 |
| | 0.5 | 55.2 | 17.1 | 53.8 | 22.7 |
| | 1.0 | 54.4 | 23.9 | 53.4 | 29.1 |
| | 5.0 | 46.5 | 57.2 | 47.3 | 62.2 |
| | 10.5 | 38.0 | 84.2 | 39.3 | 90.3 |
| | 20.0 | 19.7 | 125.9 | 21.8 | 134.0 |
| La₂O₃ | 0.1 | 57.2 | 9.8 | 18.4 | 15.1 |
| | 0.5 | 53.5 | 16.9 | 49.6 | 17.0 |
| | 1.0 | 51.5 | 25.0 | 50.5 | 23.2 |
| | 5.0 | 46.2 | 94.7 | 44.6 | 55.7 |
| | 10.0 | 34.8 | 110.8 | 36.2 | 93.0 |
| | 20.0 | 25.5 | 172.4 | 18.6 | 107.6 |
| CeO₂ | 0.1 | 57.1 | 10.1 | 23.5 | 21.5 |
| | 0.5 | 57.4 | 19.2 | 45.2 | 25.5 |
| | 1.0 | 56.1 | 29.1 | 48.1 | 33.8 |
| | 5.0 | 48.8 | 93.6 | 45.2 | 106.4 |
| | 10.0 | 42.3 | 170.5 | 39.6 | 196.6 |
| | 20.0 | 27.2 | 311.6 | 24.4 | 359.4 |
| MgO | 0.1 | 51.0 | 32.0 | 21.0 | 65.0 |
| | 0.5 | 35.0 | 110.0 | 31.0 | 90.0 |
| | 1.0 | 30.0 | 162.0 | 30.0 | 150.0 |
| | 5.0 | 21.0 | 250.0 | 23.0 | 230.0 |
| | 10.0 | 19.0 | 300.0 | 22.0 | 290.0 |
| | 20.0 | 18.0 | 305.0 | 20.0 | 300.0 |
| NiO | 0.1 | 42.0 | 11.0 | 12.0 | 15.0 |
| | 0.5 | 28.0 | 39.0 | 26.0 | 35.0 |
| | 1.0 | 23.0 | 66.0 | 21.0 | 58.0 |
| | 5.0 | 7.9 | 140.0 | 8.1 | 130.0 |
| | 10.0 | 6.0 | 195.0 | 6.3 | 180.0 |
| | 20.0 | 4.0 | 235.0 | 4.3 | 210.0 |
| ZnO | 0.1 | 56.0 | 95 | 5.6 | 20.0 |
| | 0.5 | 41.0 | 31.0 | 32.0 | 30.0 |
| | 1.0 | 26.7 | 48.0 | 34.3 | 46.0 |
| | 5.0 | 8.0 | 80.0 | 9.0 | 87.0 |
| | 10.0 | 5.5 | 110.0 | 6.5 | 120.0 |
| | 20.0 | 3.5 | 170.0 | 4.5 | 180.0 |
| Al₂O₃ | 0.1 | 39.0 | 290.0 | 15.0 | 78.0 |
| | 0.5 | 20.0 | 840.0 | 15.0 | 720.0 |
| | 1.67 | 12.9 | 1200.0 | 12.5 | 1100.0 |
| | 5.0 | 10.8 | 1800.0 | 10.5 | 1300.0 |
| | 10.0 | 9.4 | 2500.0 | 8.0 | 1700.0 |
| | 20.0 | 8.5 | 2900.0 | 7.1 | 2100.0 |
| Ga₂O₃ | 0.1 | 60.0 | 15.0 | 56.0 | 26.0 |
| | 0.5 | 67.0 | 36.0 | 54.0 | 33.0 |
| | 1.0 | 71.0 | 45.0 | 50.0 | 46.0 |
| | 5.0 | 52.0 | 86.0 | 43.0 | 71.0 |
| | 10.0 | 27.0 | 100.0 | 23.0 | 88.0 |
| | 20.0 | 12.0 | 120.0 | 11.0 | 98.0 |
| In₂O₃ | 0.1 | 32.0 | 20.0 | 30.0 | 37.0 |
| | 0.5 | 28.0 | 56.0 | 25.0 | 53.0 |
| | 1.0 | 27.0 | 82.0 | 24.0 | 71.0 |
| | 5.0 | 13.1 | 140.0 | 11.9 | 130.0 |
| | 10.0 | 9.2 | 160.0 | 7.6 | 150.0 |
| | 20.0 | 6.0 | 170.0 | 5.1 | 165.0 |
| Mn₂O₃ | 0.1 | 53.0 | 650.0 | 13.0 | 40.0 |
| | 0.5 | 33.0 | 160.0 | 31.0 | 130.0 |
| | 1.0 | 30.5 | 52.0 | 29.0 | 48.0 |
| | 5.0 | 14.0 | 110.0 | 13.0 | 103.0 |
| | 10.0 | 9.8 | 150.0 | 9.2 | 140.0 |
| | 15.0 | 5.3 | 175.0 | 5.1 | 190.0 |
| Cr₂O₃ | 0.1 | 35.5 | 23.0 | 16.0 | |
| | 0.68 | 23.4 | 18.7 | 23.3 | 19.5 |
| | 2.0 | 23.0 | 23.0 | 23.0 | 23.0 |
| | 5.0 | 19.0 | 39.0 | 20.0 | 35.0 |
| | 10.0 | 13.5 | 64.0 | 16.5 | 53.0 |
| | 15.0 | 8.0 | 88.0 | 13.5 | 74.0 |
| Li₂O | 0.43 | 27.3 | 55.0 | 23.9 | 67.0 |
| WO₃ | 1.3 | 38.3 | 15.5 | 35.4 | 17.2 |
| MoO₃ | 0.9 | 42.1 | 12.1 | 38.2 | 14.6 |
| SiO₂ | 1.0 | 23.7 | 39.4 | 21.2 | 42.0 |
| GeO₂ | 0.8 | 25.6 | 34.1 | 22.7 | 37.8 |
| Na₂O | 0.45 | 28.1 | 63.4 | 25.3 | 69.5 |
| K₂O | 0.7 | 33.2 | 98.1 | 31.0 | 103.2 |

Table 2

| Additives | | | | Sensitivity ($R_A/R_G$) | Electrical resistance in air containing 1 vol % propane ($R_G$) | after heating at 400° C for 1000 hrs. | |
|---|---|---|---|---|---|---|---|
| | | | | | | $R_A/R_G$ | $R_G$(KΩ) |
| SnO₂ 1.0 | mol% | TiO₂ 1.0 | mol% | 57.5 | 12.5 (KΩ) | 58.2 | 12.3 |

Table 2-continued

| | | | | | | |
|---|---|---|---|---|---|---|
| 3.0 | | 5.0 | | 52.3 | 53.6 | 50.1 | 53.8 |
| Eu$_2$O$_3$ 1.0 mol% | La$_2$O$_3$ 1.0 | mol% | | 52.3 | 32.5 | 51.2 | 35.2 |
| Eu$_2$O$_3$ 0.5 mol% | CeO$_2$ 1.0 | mol% | | 50.8 | 47.6 | 48.7 | 49.3 |
| La$_2$O$_3$ 1.0 mol% | CeO$_2$ 2.0 | mol% | | 47.0 | 78.3 | 46.1 | 80.6 |
| SiO$_2$ 0.29 mol% | GeO$_2$ 0.34 | mol% | | 22.8 | 62.7 | 22.7 | 67.9 |

Table 3

| Additives | | | | | | Sensitivity ($R_A/R_G$) | Electrical resistance in air containing 1 vol % propane ($R_G$) | after heating at 400° C for 1000 hrs. | |
|---|---|---|---|---|---|---|---|---|---|
| | | | | | | | | $R_A/R_G$ | $R_G$(KΩ) |
| Eu$_2$O$_3$ 0.5 | mol% | La$_2$O$_3$ 0.5 | mol% | CeO$_2$ 1.0 | mol% | 48.5 | 55.9 (KΩ) | 44.2 | 57.1 |
| 2.0 | | 0.5 | | 0.5 | | 45.9 | 54.8 | 46.5 | 53.2 |

Table 4

| Additives (mol %) | | Sensitivity ($R_A/R_G$) | Electrical resistance in air containing 0.5 vol % isobutane | after heating at 400° C for 1000 hrs. | |
|---|---|---|---|---|---|
| | | | | $R_A/R_G$ | $R_G$(kΩ) |
| WO$_3$ | 0.1 | 20.3 | 8.9 | 14.5 | 14.7 |
| | 0.3 | 22.1 | 5.8 | 18.2 | 8.0 |
| | 0.7 | 23.2 | 4.7 | 20.6 | 5.7 |
| | 3.0 | 29.1 | 2.7 | 28.0 | 2.9 |
| | 10.0 | 31.5 | 2.0 | 29.8 | 2.0 |
| | 25.0 | 7.8 | 1.6 | 4.2 | 1.7 |
| | 40.0 | 3.5 | 1.5 | 2.3 | 1.6 |
| Li$_2$O | 0.1 | 20.2 | 8.8 | 15.5 | 14.0 |
| | 0.3 | 21.0 | 8.5 | 18.8 | 10.2 |
| | 0.7 | 21.6 | 8.3 | 20.5 | 9.1 |
| | 3.0 | 24.6 | 7.2 | 23.6 | 7.3 |
| | 10.0 | 8.4 | 6.1 | 7.7 | 6.7 |
| | 20.0 | 3.0 | 5.3 | 2.1 | 5.5 |
| Na$_2$O | 0.1 | 20.5 | 9.4 | 14.7 | 14.8 |
| | 0.3 | 21.4 | 9.0 | 19.2 | 10.5 |
| | 0.7 | 22.2 | 8.9 | 21.1 | 9.8 |
| | 3.0 | 25.0 | 7.6 | 24.2 | 8.4 |
| | 10.0 | 9.1 | 6.5 | 7.8 | 6.9 |
| | 20.0 | 3.0 | 5.7 | 2.5 | 6.0 |
| K$_2$O | 0.1 | 21.2 | 9.8 | 16.0 | 17.0 |
| | 0.3 | 22.2 | 9.5 | 19.4 | 10.8 |
| | 0.7 | 23.9 | 9.0 | 21.8 | 10.2 |
| | 3.0 | 23.4 | 8.2 | 21.0 | 8.3 |
| | 10.0 | 8.2 | 6.7 | 7.4 | 7.5 |
| | 20.0 | 4.1 | 6.0 | 2.7 | 6.9 |
| SiO$_2$ | 0.1 | 20.0 | 8.2 | 13.1 | 13.1 |
| | 0.3 | 19.6 | 6.4 | 15.0 | 9.0 |
| | 0.7 | 19.8 | 6.1 | 16.2 | 7.8 |
| | 3.0 | 19.8 | 6.1 | 16.2 | 7.8 |
| | 3.0 | 21.1 | 5.3 | 19.4 | 6.1 |
| | 10.0 | 22.0 | 5.2 | 22.0 | 5.7 |
| | 25.0 | 9.4 | 5.1 | 8.0 | 6.1 |
| | 40.0 | 4.5 | 5.1 | 2.0 | 6.5 |
| GeO$_2$ | 0.1 | 20.6 | 9.0 | 14.1 | 14.5 |
| | 0.3 | 20.5 | 7.2 | 15.8 | 10.0 |
| | 0.7 | 20.6 | 6.5 | 16.7 | 8.7 |
| | 3.0 | 21.4 | 6.0 | 19.3 | 6.7 |
| | 10.0 | 22.1 | 5.7 | 21.8 | 6.3 |
| | 25.0 | 10.0 | 5.3 | 8.1 | 6.3 |
| | 40.0 | 4.7 | 5.2 | 2.1 | 6.3 |
| MoO$_3$ | 0.1 | 21.8 | 8.8 | 14.2 | 13.3 |
| | 0.3 | 23.0 | 5.7 | 18.0 | 7.4 |
| | 0.7 | 25.0 | 4.3 | 20.0 | 5.6 |
| | 3.0 | 28.3 | 2.5 | 26.8 | 2.7 |
| | 10.0 | 29.5 | 1.6 | 28.7 | 1.8 |
| | 25.0 | 8.0 | 1.3 | 4.0 | 1.5 |
| | 40.0 | 2.9 | 1.2 | 2.1 | 1.4 |
| NiO | 3.3 | 28.6 | 2.87 | 28.5 | 2.92 |
| Mn$_2$O$_3$ | 3.0 | 18.5 | 4.01 | 18.2 | 4.35 |
| TiO$_2$ | 3.1 | 19.8 | 1.75 | 20.3 | 1.83 |
| BaO | 3.0 | 13.1 | 19.8 | 11.8 | 23.3 |
| La$_2$O$_3$ | 3.3 | 22.6 | 6.6 | 21.7 | 7.5 |

Table 5

| Additives | | | | Sensitivity ($R_A/R_G$) | Electrical resistance in air containing 0.5 vol.% isobutane ($R_G$) | after heating at 400° C for 1000 hrs. | |
|---|---|---|---|---|---|---|---|
| | | | | | | $R_A/R_G$ | $R_G$(KΩ) |
| WO$_3$ 0.1 | mol % | MoO$_3$ 0.1 | mol % | 21.3 | 7.3 (KΩ) | 14.7 | 11.0 |
| 0.3 | | 0.7 | | 24.7 | 3.9 | 21.5 | 4.8 |
| 0.7 | | 3.0 | | 29.0 | 2.3 | 28.7 | 2.2 |
| 7.0 | | 8.0 | | 27.3 | 1.7 | 24.3 | 1.8 |
| 30.0 | | 10.0 | | 3.2 | 1.4 | 2.1 | 1.6 |
| Li$_2$O 0.1 | | Na$_2$O 0.1 | | 20.6 | 9.0 | 16.6 | 12.5 |
| Li$_2$O 0.7 | | K$_2$O 0.7 | | 24.2 | 8.5 | 23.5 | 8.8 |
| Na$_2$O 10.0 | | K$_2$O 3.0 | | 6.1 | 6.4 | 5.4 | 6.7 |
| SiO$_2$ 0.1 | | GeO$_2$ 0.03 | | 20.0 | 8.0 | 13.7 | 12.2 |
| 0.7 | | 0.3 | | 20.2 | 6.2 | 17.3 | 7.7 |
| 3.0 | | 7.0 | | 21.8 | 5.3 | 21.6 | 5.9 |
| 10.0 | | 20.0 | | 9.4 | 5.2 | 8.0 | 6.1 |
| In$_2$O$_3$ 1.6 | | Ga$_2$O$_3$ 1.6 | | 13.9 | 4.1 | 12.1 | 5.2 |
| Na$_2$O 0.05 | mol % | GeO$_2$ 0.05 | mol % | 20.6 | 9.2 | 14.5 | 14.6 |
| 0.7 | | 0.3 | | 22.3 | 7.3 | 20.1 | 8.5 |
| 3.7 | | 7.0 | | 20.0 | 5.9 | 19.2 | 6.5 |
| 7.0 | | 10.0 | | 18.1 | 5.8 | 17.5 | 6.4 |
| 20.0 | | 20.0 | | 4.5 | 5.7 | 3.6 | 6.3 |
| GeO$_2$ 0.1 | mol % | WO$_3$ 0.05 | mol % | 20.6 | 8.0 | 14.7 | 11.9 |
| 0.7 | | 1.3 | | 23.7 | 4.3 | 22.1 | 5.8 |

Table 5-continued

| Additives | | Sensitivity ($R_A/R_G$) | Electrical resistance in air containing 0.5 vol.% isobutane ($R_G$) | after heating at 400° C for 1000 hrs. | |
|---|---|---|---|---|---|
| | | | | $R_A/R_G$ | $R_G(K\Omega)$ |
| 7.0 | 10.0 | 21.1 | 3.2 | 20.4 | 3.5 |
| 25.0 | 10.0 | 6.4 | 2.9 | 5.1 | 3.5 |
| 10.0 | 30.0 | 3.5 | 2.8 | 2.4 | 3.7 |

Table 6

| Additives | | | Sensitivity ($R_A/R_G$) | Electrical resistance in air containing 0.5 vol %. isobutane($R_G$) | after heating at 400° C for 1000 hrs. | |
|---|---|---|---|---|---|---|
| | | | | | $R_A/R_G$ | $R_G(K\Omega)$ |
| $Li_2O$ | $Na_2O$ | $K_2O$ | | | | |
| 0.1 mol% | 0.7 mol% | 1.3 mol% | 24.6 | 8.2 (KΩ) | 23.6 | 8.5 |
| 5.0 | 2.0 | 2.0 | 9.0 | 6.7 | 8.0 | 6.9 |
| 5.0 | 10.0 | 5.0 | 4.0 | 5.8 | 2.4 | 6.7 |
| $Na_2O$ | $GeO_2$ | $WO_3$ | | | | |
| 0.05 mol% | 0.05 mol% | 0.05 mol% | 20.7 | 8.7 | 15.1 | 12.9 |
| 0.1 | 0.2 | 0.7 | 22.4 | 5.6 | 19.8 | 7.4 |
| 0.7 | 3.3 | 2.0 | 25.9 | 4.8 | 24.9 | 5.6 |
| 7.0 | 10.0 | 3.0 | 17.3 | 3.7 | 14.5 | 5.1 |
| 20.0 | 10.0 | 10.0 | 4.1 | 3.5 | 3.2 | 4.7 |
| 10.0 | 10.0 | 20.0 | 3.5 | 3.1 | 2.7 | 3.6 |

What is claimed is:

1. A reducing gas sensor comprising a gas sensitive element composed of, as a main constituent, γ-ferric oxide (γ-$Fe_2O_3$) and, as an additive, at least one member selected from the group consisting of $WO_3$, $MoO_3$, $SiO_2$, $GeO_2$, $Li_2O$, $Na_2O$, $K_2O$, CaO, SrO, BaO, $Eu_2O_3$, $La_2O_3$, $CeO_2$, $Al_2O_3$, $Ga_2O_3$, $In_2O_3$, $SnO_2$, $TiO_2$, MgO, NiO, ZnO, $Mn_2O_3$ and $Cr_2O_3$, a pair of electrodes on said sensitive element and a heater element adjacent said element, whereby when said gas sensitive element is heated to an elevated temperature it undergoes a rapid decrease in electrical resistance upon coming in contact with an atmosphere containing a reducing gas.

2. A reducing gas sensor according to claim 1, wherein said additive is 0.1 to 40.0 mol % of at least one member selected from the group consisting of $WO_3$ and $MoO_3$.

3. A reducing gas sensor according to claim 1, wherein said additive is 0.1 to 40.0 mol % of at least one number selected from the group consisting of $SiO_2$ and $GeO_2$.

4. A reducing gas sensor according to claim 1, wherein said additive is 0.1 to 10.0 mol % of at least one member selected from the group consisting of $Li_2O$, $Na_2O$ and $K_2O$.

5. A reducing gas sensor according to claim 1, wherein said additive is 0.1 to 20.0 mol % of at least one member selected from the group consisting of CaO, SrO and BaO.

6. A reducing gas sensor according to claim 1, wherein said additive is 0.1 to 20.0 mol % of at least one member selected from the group consisting of $Eu_2O_3$, $La_2O_3$ and $CeO_2$.

7. A reducing gas sensor according to claim 1, wherein said additive is 0.1 to 20.0 mol % of at least one member selected from the group consisting of $Al_2O_3$, $Ga_2O_3$ and $In_2O_3$.

8. A reducing gas sensor according to claim 1, wherein said additive is 0.1 to 30.0 mol % of at least one member selected from the group consisting of $SnO_2$ and $TiO_2$.

9. A reducing gas sensor according to claim 1, wherein said additive is 0.1 to 15.0 mol % of at least one member selected from the group consisting of MgO, NiO and ZnO.

10. A reducing gas sensor according to claim 1, wherein said additive is 0.1 to 15.0 mol % of at least one member selected from the group consisting of $Mn_2O_3$ and $Cr_2O_3$.

11. A reducing gas sensor according to claim 1, wherein said additive is 0.1 to 20.0 mol % of at least one member selected from the group consisting of SrO and BaO or 0.1 to 15.0 mol % of MgO.

* * * * *